United States Patent [19]
Hall et al.

[11] Patent Number: 5,464,960
[45] Date of Patent: Nov. 7, 1995

[54] LASER CALIBRATION DEVICE

[75] Inventors: Deborah K. Hall, Menlo Park, Calif.;
Erik Rencs, Baltimore, Md.

[73] Assignee: Iatrotech, Inc., Menlo Park, Calif.

[21] Appl. No.: 150,603

[22] Filed: Nov. 10, 1993

Related U.S. Application Data

[63] Continuation-in-part of Ser. No. 3,521, Jan. 12, 1993, Pat. No. 5,261,822.

[51] Int. Cl.$^6$ .................................................. B23K 26/02
[52] U.S. Cl. ................................. 219/121.6; 219/121.69; 434/271
[58] Field of Search ........................... 219/121.6, 121.61, 219/121.62, 121.83, 121.68, 121.69, 121.67, 121.7, 121.71, 121.72; 606/4, 5, 6; 364/474.08; 434/271

[56] References Cited

U.S. PATENT DOCUMENTS

| | | | |
|---|---|---|---|
| 4,087,672 | 5/1978 | Yi | 219/121.62 |
| 4,414,059 | 11/1983 | Blum et al. | 219/121.85 |
| 4,545,018 | 10/1985 | Clements et al. | 364/474.08 |
| 4,825,034 | 4/1989 | Auvert et al. | 219/121.72 |
| 4,866,243 | 9/1989 | Sakane et al. | 606/4 |
| 4,918,611 | 4/1990 | Shyu et al. | 364/474.08 |
| 5,091,626 | 2/1992 | Lewis et al. | 219/121.69 |
| 5,166,492 | 11/1992 | Rivera | 219/121.68 |
| 5,211,805 | 5/1993 | Srinivasan | 219/121.61 |

FOREIGN PATENT DOCUMENTS

| | | | |
|---|---|---|---|
| 503802 | 9/1992 | European Pat. Off. | 606/4 |
| 557719 | 9/1993 | European Pat. Off. | 219/121.61 |
| 4-81285 | 3/1992 | Japan | 219/121.61 |

*Primary Examiner*—Geoffrey S. Evans
*Attorney, Agent, or Firm*—Henri J. A. Charmasson; John D. Buchaca

[57] ABSTRACT

A phantom cornea for calibrating surgical lasers is formed by superimposition of thin-films of alternating colors. After ablation by a laser beam, the resulting spherical cavity appears as a pattern of nested circles whose concentricity and spacing reflect the alignment and intensity of the laser beam. These patterns can be visually or instrumentally analyzed to determine the proper setting of the laser. A monolayer or multi-layer thin film is used to determine, not only the ablative power of a laser beam, but also the variation of the ablative power over the full breadth of the beam by observing the area impinged by the beam between successive laser pulses. The calibration cornea can be planar, or arcuate to mimic the natural cornea. The calibration cornea may be mounted in a phantom eyeball including a removable iris of small diameter which constitutes a convenient target for the alignment of the laser beam.

16 Claims, 4 Drawing Sheets

LASER CALIBRATION DEVICE

Prior Application

This is a continuation-in-part application of copending application Ser. No. 08/003,521 filed Jan. 12, 1993 to be issued as U.S. Pat. No. 5,261,822.

FIELD OF THE INVENTION

This invention relates to laser use in ophthalmic surgery to either remove diseased tissue from the front of the cornea or to change the curvature of the cornea by tissue removal. More specifically, this invention relates to artificial tissue used to calibrate the intensity of a surgical laser before use on the patient.

BACKGROUND OF THE INVENTION

Prior to this invention, surgical lasers used on corneal tissue were calibrated by first ablating some material on the surface of a polymethyl-methacrylate (PMMA) card. The resulting concave cavity on the surface of the card created a negative-diopter lens. The power of that lens was then measured by means of a lensometer. If the reading differed from a predetermined value, typically −4 diopters, the laser intensity was adjusted by a calibration factor corresponding to the difference between the lensometer reading and the desired surgical power of the laser.

This cumbersome calibration method has two major drawbacks. In the first place, the lensometer provides an approximate reading of the curvature of the ablation. If the ablation was aspheric, wherein the power at the center of the ablation was different than the power at the periphery of it, the lensometer would only give a reading close to the power reading of the central part of the ablation. In the second place, lensometers are not very accurate and exhibit typical errors of up to 6 percent between two readings of the same ablated card. The best accuracy obtainable under this procedure is 0.25 diopters centered at −4 diopters, reflecting a 12 percent margin of error.

This prior art calibrating process for surgical laser is not only cumbersome and inaccurate, but also lengthy and ill-adapted to the environment of an operating room.

A more precise method is needed in order to evaluate the consistency of the ablation over the targeted corneal surface area. Physiologically, the human vision system cannot resolve closely spaced multiple focal points. The system translates the multi-focal data as an understandable, but not necessarily accurate image. The prior art does not provide any reliable method for verifying the regularity of the laser ablative power across the entire beam.

SUMMARY OF THE INVENTION

The principal and secondary objects of this invention are to provide a convenient and expeditious method for calibrating a laser used to ablate corneal tissue whereby the surgeon can quickly calibrate or recalibrate the laser, or determine if the ablative power deviation of the laser across the targeted area is within a tolerable margin, before and during surgery by visual inspection and/or instrumental measurements. These and other objects are achieved by using either a monolayer or multi-layer thin film made of PMMA or other ablatable material. According to the first method, the laser is aimed at a monolayer thin film spin-coated over a crown glass slide. The number of laser pulses needed to remove the coating over an area of the film, signaled by a sudden fluorescence as the laser reaches the underlying glass, is used as a calibration factor. This calibration factor is obtained by dividing the thickness of the monolayer film by the number of pulses used to reach fluorescence. Calibration factors are obtained for the various areas of the targeted surface until the entire area becomes fluorescent. The spread between these various factors provides a fairly accurate mapping of the ablative characteristics of the laser beam across its entire width. In multi-layer films, the layers have distinctive colors or optical characteristics and their thicknesses are adjusted to create a symmetrical pattern of concentric circles when a spherical cavity is ablated by a laser beam normal to film surfaces. A misalignment of the laser beam results in an eccentricity of the pattern circles. Any deviation from a desired intensity causes a change in the radius of the ablated cavity. This results in changes in the width of the pattern circles which can be detected by visual inspection. Colored and fluorescent doping of the layers can be used to facilitate the detection of variations in the patterns of circles created by the laser ablation.

DESCRIPTION OF THE PREFERRED EMBODIMENT OF THE INVENTION

Figure 1:
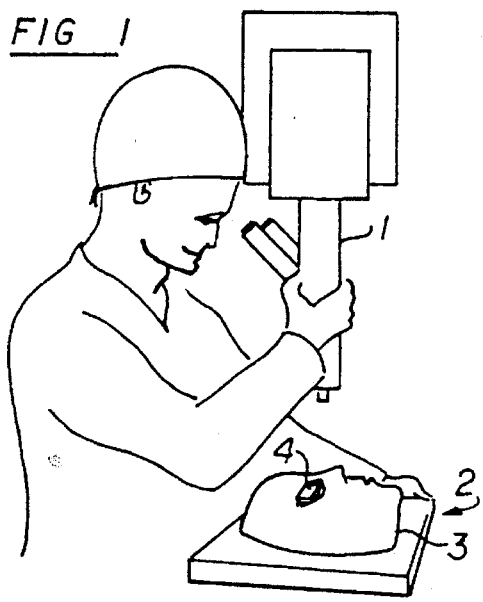
FIG. 1 is an illustration of a surgical laser and calibration block according to the invention.

Referring now to the drawing, there is shown in FIG. 1 a surgical laser 1 being applied to a ophthalmic phantom 2 comprising a simulated human face 3 including a calibration block 4 according to the invention installed in the ocular cavity of the ophthalmic phantom. The laser may be an excimer, solid-state or holmium type such as those commonly used to remove diseased corneal tissue in therapeutic surgery, or to change the curvature of the cornea in corrective surgery. The phantom 2 may be of the type disclosed in U.S. Pat. No. 4,762,495 and U.S. Pat. No. 4,865,551.

Figure 2:
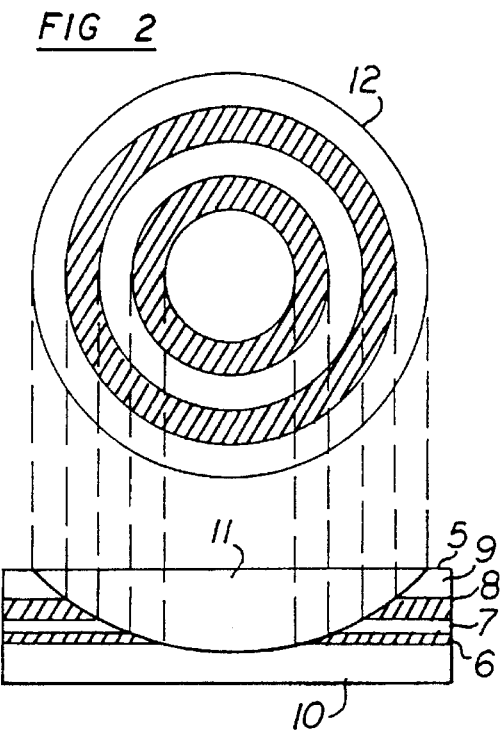
FIG. 2 is a diagram illustrating the formation of the pattern of circles created by the laser ablation on the surface of the calibration block.
Figure 5:
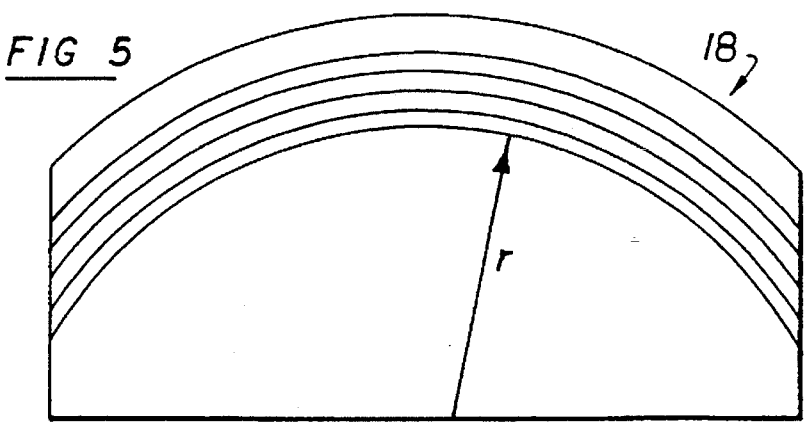
FIG. 5 is a cross-sectional view of an alternate embodiment of the calibration block.

The calibration block may have a planar surface such as the one illustrated in FIG. 2 or may be curved to simulate a human cornea as the one illustrated in FIG. 5.

Figure 4:
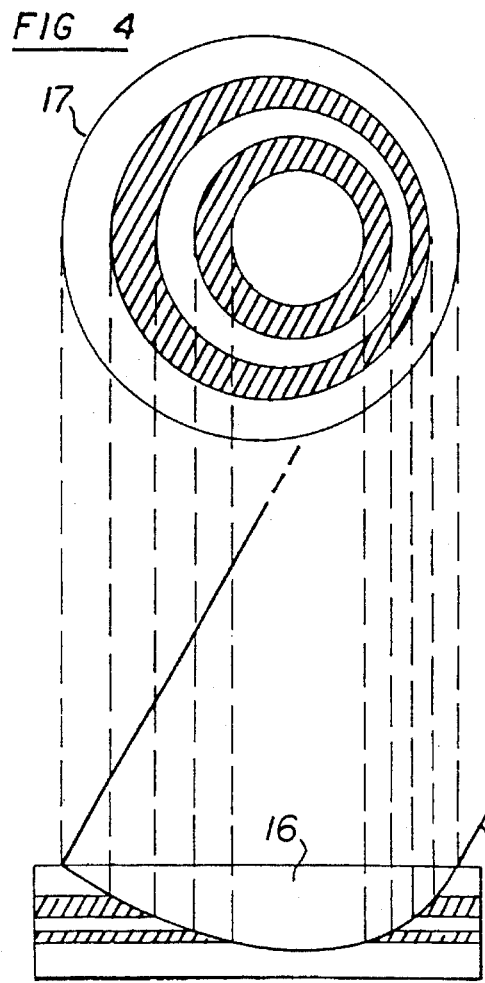
FIG. 4 is a diagram illustrating the eccentricity of the circle pattern due to a misalignment of the laser.
Figure 3:
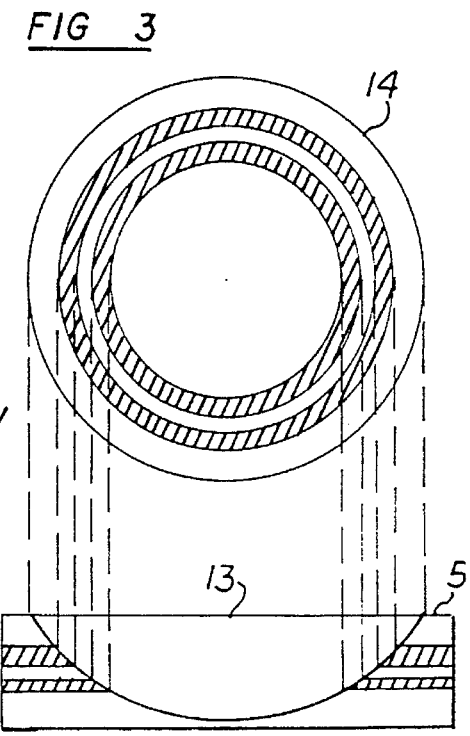
FIG. 3 is a diagram illustrating the variation of circles-width resulting from an increase in the laser intensity.

The calibration block 5 illustrated in FIGS. 2–4 comprises a plurality of thin-films or layers 6, 7, 8 and 9 of PMMA material over a substrate 10 of the same material. The layers or thin films have thicknesses that increase progressively from the most distal, bottom layer 6 to the top layer 9. The layer thicknesses are adjusted so that when the concave cavity 11 ablated by a laser beam orthogonally striking the surface of the block 5, is viewed from above, it creates a pattern 12 of concentric circles which are evenly spaced from one another. Table 1 lists the series of twelve layer thicknesses calculated to exhibit such a concentric pattern for a cavity corresponding to a lens power of −4 diopters. Such a cavity corresponds to the typical laser intensity required for corneal ablation. Other sets of layer thicknesses may be calculated according to the following formula:

$$t(i) = \sqrt{R^2 - \left[(N-i)\frac{R}{N}\right]^2} - \sum_{j=0}^{j=i-1} tj$$

wherein $$R = \frac{0.36}{P} \, 1000$$

P is the dioptric power of the cavity-formed lens.
t is the thickness of each layer.
N is the number of layers over a full quadrant.
i is the layer ranking.

TABLE I

| Layer | | POWER −4 RADIUS 90 M Thickness (micron) |
|---|---|---|
| Bottom | 1 | 0.347 |
| | 2 | 1.042 |
| | 3 | 1.736 |
| | 4 | 2.736 |
| | 5 | 3.125 |
| | 6 | 3.82 |
| | 7 | 4.515 |
| | 8 | 5.209 |
| | 9 | 5.904 |
| | 10 | 6.6 |
| | 11 | 7.245 |
| Top | 12 | 7.99 |

FIG. 2 illustrates the cavity 13 formed by a laser beam of greater intensity that yields a corresponding lens of greater negative power. It should be noted that the corresponding top plan view pattern 14 has circles with asymmetrical spacing. Accordingly, the improper setting of the laser intensity can be quickly detected by visual inspection of the circle pattern.

In the illustration of FIG. 4, the block 5 is ablated by a misaligned, i.e. oblique laser beam 15. The misalignment is purposely exaggerated in the illustration for the sake of clarity. The floor of the resulting cavity 16 is aspheric, resulting in a pattern 17 of eccentric circles.

The visual or instrumental inspection of the circle pattern can be facilitated by giving the layers different optical properties. For instance, each layer may be doped with a hue different from the hue used to dope any other contiguous layer. Alternately, every other layer may be doped with fluorescin or ammonia in order to create a luminescent glow under light. The refractive or other physical properties of the layers may be varied by using the same or different material with distinct molecular weights.

A simple method for calibrating the laser in terms of number of pulses necessary to abalte through a desired thickness of material consists in programming the laser to cut a conic section into the multi-layer device comprising alternate fluorescent and non-fluorescent layers. As one fluorescing layer is penetrated the laser begins ablating a non-fluorescing material. This transition is marked by a large decrease of light emitted from the ablation surface. Viewed from above (through the microscope) the perfect laser will produce a pattern of concentric circles, alternating as fluorscent and non-fluorescent bands. Properly illuminated, the circles are easy to see and small deviations of laser intensity are easily recognized by the human observer or analyzed by a computer. The ablation pattern is then stored indefinitely and can be analyzed at the operator's leisure. By knowing the depth of each layer and counting the laser pulses delivered to the edge of the concentric bands the calibration factors can be quickly determined.

The layers or thin films can be formed over the substrate according to methods well-known in the art of integrated circuit fabrication such as epitaxial growth or vapor disposition. A near-molecular thickness of film can be achieved by organic deposition of Langmuir-Blodgett films. Other processes such as spin-coating and flame-spraying and flame-spraying may be used to build the block layers.

In the calibrating block 18 illustrated in FIG. 5, the layers are built upon a substrate having a convex spherical surface with a radius of approximately 1 centimeter corresponding to the radius of a human cornea.

As in the first embodiment, the layer thicknesses dan be calculated to yield a concentric and symmetrical top plan-view pattern according to the following formula:

$$t(i) = \sqrt{\left(\frac{iR}{N}\right)^2 + \left[r^2 - \sqrt{R^2 - \left(\frac{iR}{N}\right)^2}\right]^2} - (r-R) - \sum_{j=0}^{j=i-1} tj$$

wherein r is the calibration block radius.

Figure 6:
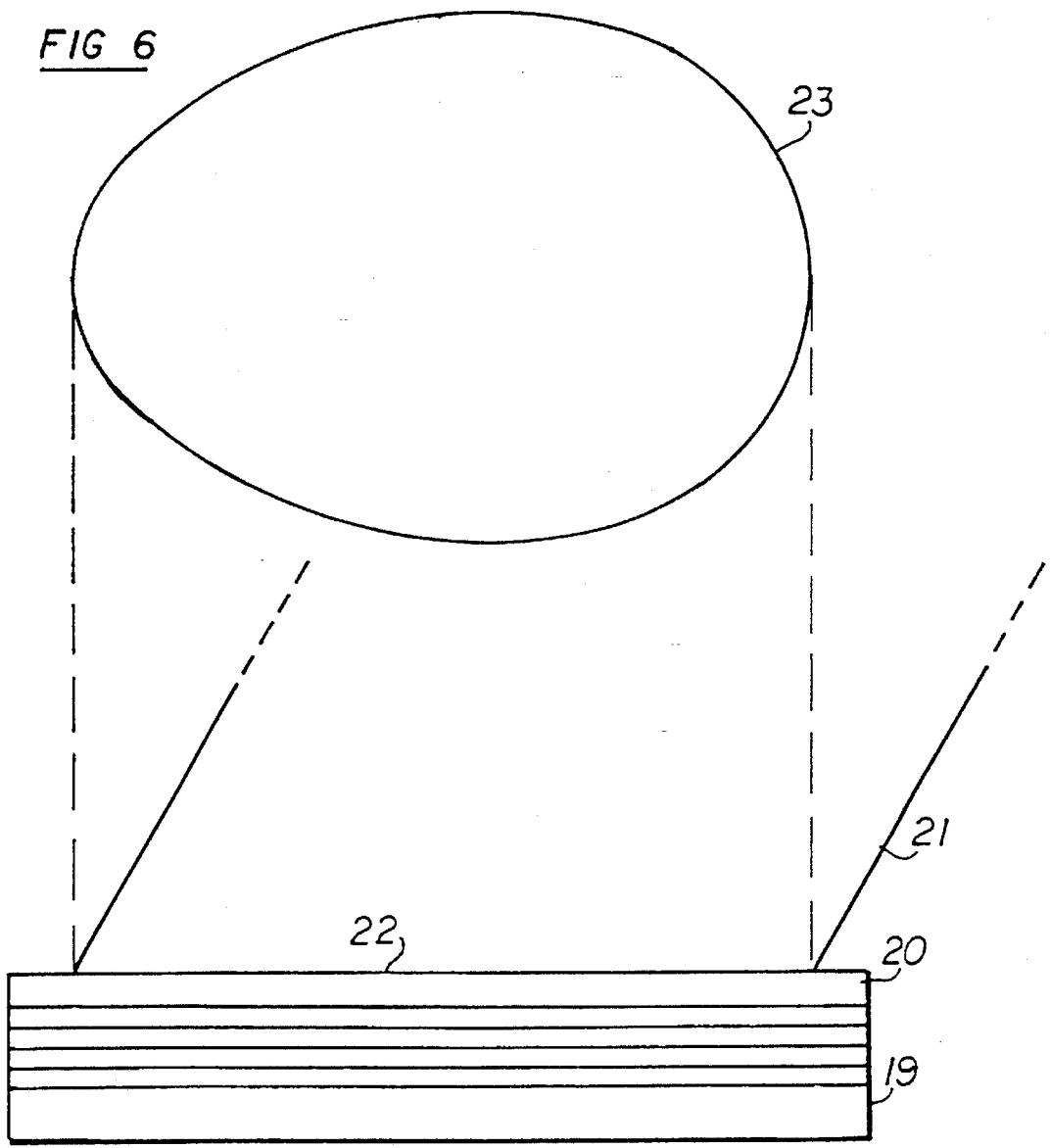
FIG. 6 illustrates a fluorescent pattern resulting from a misalignment of the laser.

In the calibration block 19 illustrated in FIG. 6, the top layer 20 is doped with fluorescin, ammonia or other illuminescent compound. When a laser beam 21 impinges upon the top surface of the upper layer 20 it creates a luminescent spot 22. If the laser beam is oblique rather than normal, as illustrated, the luminescent spot assumes an ovoidal shape 23 rather than a perfect circular shape. The procedure can thus be used to accurately position the laser to a normal position through visual observation of the luminescent spot 22.

Although polymethyl-methacrylate (PMMA) has been used in connection with the above-described embodiments of the calibration block, other synthetic or natural materials that substantially mimic the properties of the natural cornea, such as collagen, may be used as base material.

Figure 7:
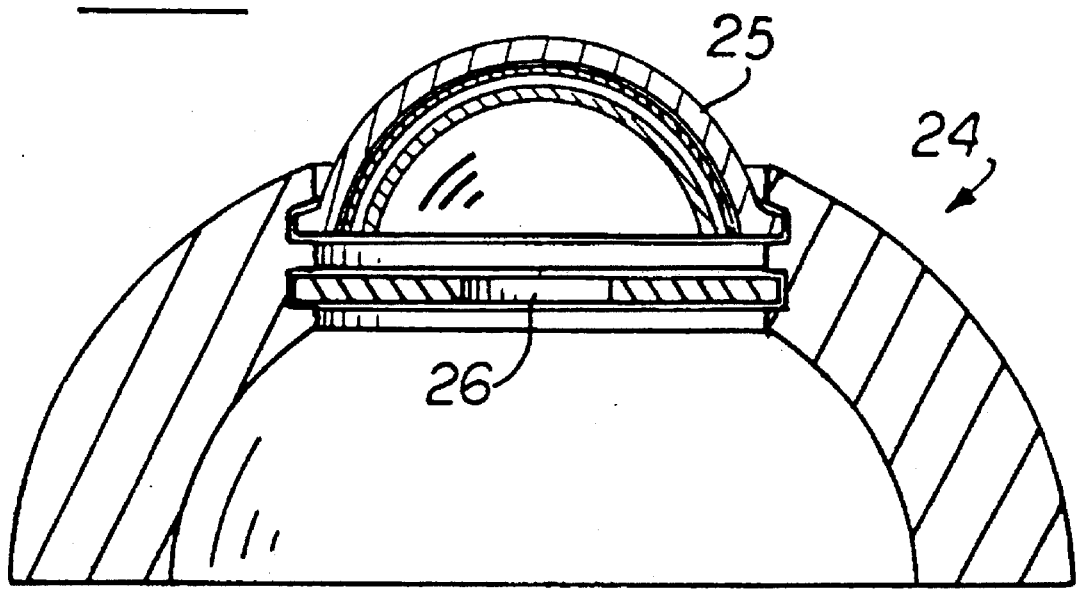
FIG. 7 is a cross-sectional view of a complex ophthalmic phantom.

FIG. 7 illustrates a ophthalmic phantom 24 of the type disclosed in U.S. Pat. Nos. 4,762,496 and 4,865,551 which can be mounted in the facial cast 2 of FIG. 1.

The phantom eye 24 is characterized by the movable, multi-layered cornea 25, and a removable iris 26 installed behind it. The cornea may be formed according to the above-described techniques to produce the symmetrical ring pattern upon laser ablation.

The removable iris 26 with a pupil diameter of approximately 2 millimeters provides a convenient target when centering the laser beam. After ablation, the iris can be removed, and the shape of the ablation can be measured with a lensometer without having to dismount the phantom cornea.

The iris 26 is preferably made in a dark color for better contrast with the fluorescent zones of the cornea.

Every other layer of the cornea, or the entire cornea in some applications, should be black in order to allow better reflection and facilitate cornea topography.

According to the alternate or complementary method of laser calibration disclosed below, a monolayer thin film is used to map the ablative power of a laser beam across the entire target area. From this mapping one may, not only determine the exact number of pulses necessary to ablate a desired thickness of material, but one may also quantify the deviation in the homogeneity of the ablative power of the laser across the impacted area.

The laser beam is aimed at a single layer thin film made by spin-coating PMMA on a precision microscope slide of crown glass. As the laser ablates through the device of depth=Y (in microns), at some pulse X the film is penetrated as evidenced by violent fluorescence. The calibration factor at these places of film penetration is then=Y/X microns/pulse. The following pulse X+1 shows an increase in area where the film has been penetrated. By subtracting the penetrated area at pulse X we can determine the calibration factor for the remaining area which=Y/X+1 microns/pulse. The single layer device can be implemented for determining accurate calibration factors at the stated depth for the surgery about to be performed. The thickness of the films may vary from 10 to 50 microns. For quick qualitative "checking" this device can give a simple "go or no go" type of answer just by observing the ablation pattern as it occurs. If the impinged upon material disappears within 1 or 2 pulses, then the laser can be considered homogeneous. A 1 or 2 pulse spread means resolution of beam accuracy of less than six percent for a 10 micron film. For a 50 micron film this resolution would be less than two percent.

If the intensity of the laser beam is not homogeneous, various patterns will be created between the time a first portion of the monolayer thin film of a constant thickness is removed and the time the thin film material is ablated from the entire area impinged upon by the laser beam. Calibration factors may be determined by simply counting how many pulses are needed to ablate each portions of the impinged area. Study of the ablation progress is best by digitization of photographs taken of the target film after each laser pulse, and analysis of the digitized image by data processing equipment. The computerized digitization of the photographs creates storable arrays of data that can be enhanced by well-known image processing techniques and quantified for easy analytical processing.

The following example is illustrated by FIGS. 8a–8f.

Keeping in mind that the object of the test is to determine how much ablatable material is removed per pulse of laser energy to be expressed in terms of micron per pulse (m/p), pictures of monolayers thin film are taken after every pulse impact on a 11 micron slide-mounted thin film 27 which can readily be implemented within a one percent variation in thickness across the entire surface of the slide 28.

Figure 8A:
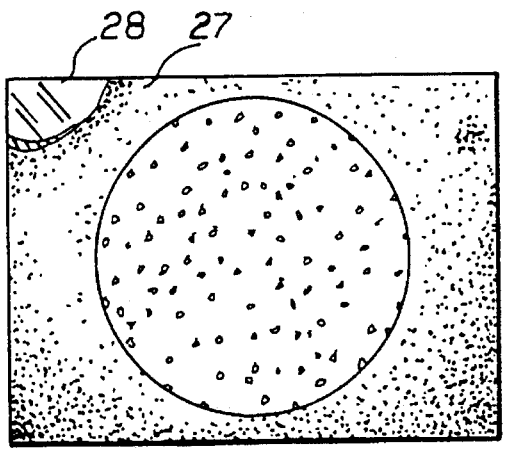
FIGS. 8a–8f are diagrammatical illustrations of the progressive ablation of a monolayer thin film calibration device by a pulsed laser beam.

FIG. 8a illustrates a pre breakthrough image somewhere around the 39th pulse.

Figure 8B:
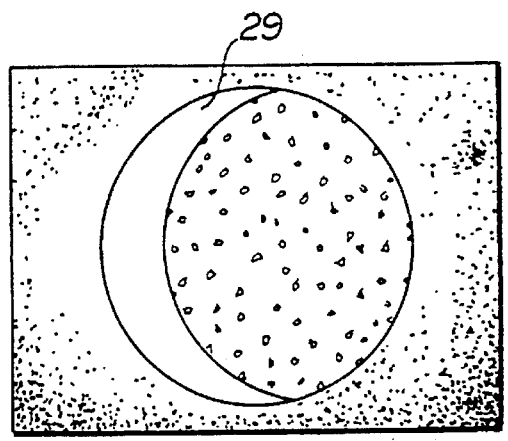

FIG. 8b shows the first breakthrough at pulse number 43. The calibration factor of the laser is=(11 microns/43 pulses) 0.256 micron/pulse for the ablated area 29.

Figure 8C:
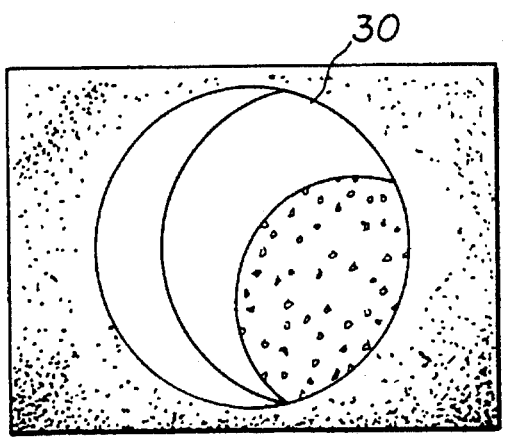

FIG. 8c corresponds to the image taken after pulse number 44. Line 30 encircles the area within which the calibration factor of the laser is (11 microns/44 pulses) 0.25 micron/pulse.

Figure 8D:
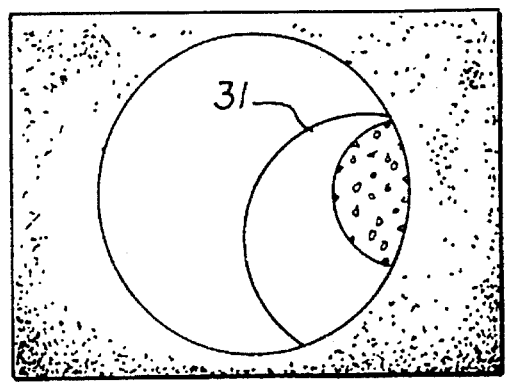

FIG. 8d reflects the image taken after pulse number 45. Line 31 encircles the area within which the calibration factor of the laser is (11 micron/45 pulses) 0.244 micron/pulse.

Figure 8E:
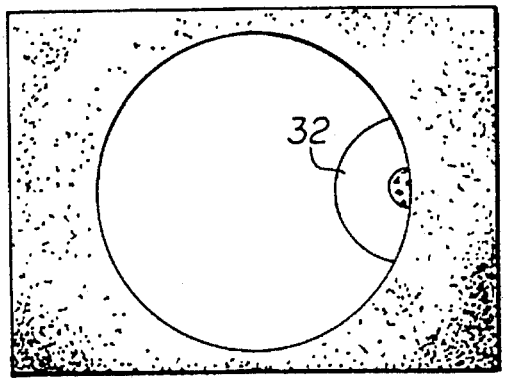
Figure 8F:
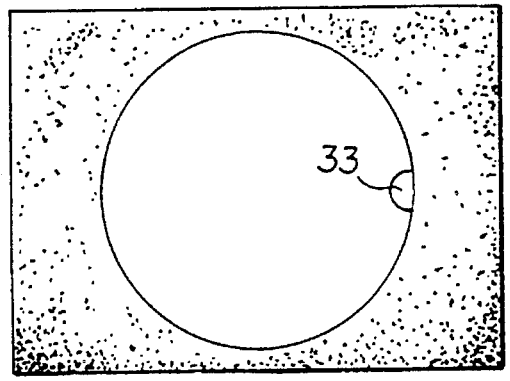

FIG. 8e represents the image taken after pulse number 46. Line 32 encircles the area within which the calibration factor of the laser is (11 micorn/46 pulses) 0.239 micron/pulse.

FIG. 9f corresponds to the image taken after pulse number 49. Line 33 encircles the area within which the calibration factor of the laser is (11 micron/49 pulses) 0.224 micron/pulse.

The range of ablation is 0.256 to 0.224 micron/pulse. The range can be described as having a (0.032/0.256) 12 percent or (0.032/0.224) 14 percent variance.

It should be understood that the above-described devices and method are not only applicable to surgical lasers used in therapeutic and refractive keratotomy, but to all types of industrial lasers used in connection with precision ablation of various materials.

While the preferred embodiments of the invention have been described, modifications can be made and other embodiments may be devised without departing from the spirit of the invention and the scope of the appended claims.

What is claimed is:

1. A method for measuring and mapping the intensity of an ablative, pulsed laser beam and using said laser beam to ablate a section of tissue to a desired depth, which comprises:

forming a target comprising at least one layer of ablatable material having a constant thickness;

aiming the pulsed laser beam at said target;

observing the effect of said beam upon an area of said target impinged upon by the laser beam;

counting the number of laser pulses necessary to ablate a first entire portion of said area;

dividing said thickness by said number to obtain a first ablating factor for said portion;

and applying to said tissue a number of laser pulses proportional to the ratio of said depth over said first ablating factor.

2. The method of claim 1 which further comprises:

counting at least one additional number of laser pulses necessary to ablate at least one entire additional portion of said areas;

dividing said thickness by said at least one additional number to obtain at least one more ablating factor; and applying to said tissue a number of laser pulse proportional to the ratio of said depth over a combination of said ablating factors.

3. The method of claim 2, wherein the step of observing comprises taking images of said target between successive laser pulses.

4. The method of claim 3, wherein said observing step further comprises breaking said images into digitized arrays.

5. The method of claim 1, wherein said layer is made of polymethylmethacrylate.

6. The method of claim 1, wherein said layer comprises a epitaxially-grown thin film.

7. The method of claim 1, wherein said layer comprises a vapor-deposited thin film.

8. The method of claim 1, wherein said layer comprises a Langmuir-Blodgett film.

9. The method of claim 1, wherein said layer comprises a spin-coated film.

10. A method for adjusting the intensity of a laser beam having a circular cross-section prior to using said beam to ablate a section of tissue, wherein said method comprises:

selecting a target having a plurality of layers of ablatable material wherein each individual layer has a constant thickness, and a different optical characteristic than any other layer contiguous to said individual layer;

exposing said target to said beam wherein said beam impinges upon an area of said target;

observing the effect of said beam upon said area;

adjusting the intensity of said beam; and successively repeating said exposing, observing and adjusting steps until said beam creates on said area a pattern of evenly spaced concentric circles.

11. The method of claim 10 which comprises using a target having a plurality of superimposed, parallel layers of synthetic material including a distal bottom layer and a proximal surface layer, wherein the thickness ti of each of said layers having a rank i from said bottom layer having a rank i=1 to said surface layer having a rank i=N is adjusted to create a pattern of concentric rings having alternate optical characteristics and equal plan view width when said target is laser-ablated along an axis normal to said layers to form a concave surface corresponding to a lens of a given diopter power P, where N is the total number of said layers.

12. The method of claim 11, wherein said target is shaped and dimensioned to simulate a human cornea.

13. The method of claim 12, wherein the thicknesses ($t_{(i)}$) of each of said layers is equal to $$\sqrt{R^2 - \left[(N-i)\frac{R}{N}\right]^2} - \sum_{j=0}^{j=i-1} tj$$

wherein $$R = \frac{0.36}{P} 1000.$$

14. The method of claim 10 wherein any particular layer has a different color than any other layer contiguous to said particular layer.

15. The method of claim 10, wherein any particular layer has a different molecular weight than any other layer contiguous to said particular layer.

16. The method of claim 10, wherein at least one of said layers is doped with a fluorescent compound.

* * * * *